United States Patent
Banju et al.

(10) Patent No.: US 11,833,472 B2
(45) Date of Patent: Dec. 5, 2023

(54) FILTRATION FILTER AND FILTRATION METHOD

(71) Applicant: Murata Manufacturing Co., Ltd., Nagaokakyo (JP)

(72) Inventors: Masaru Banju, Nagaokakyo (JP); Shusuke Yokota, Nagaokakyo (JP); Takashi Kondo, Nagaokakyo (JP)

(73) Assignee: MURATA MANUFACTURING CO., LTD., Nagaokakyo (JP)

( * ) Notice: Subject to any disclaimer, the term of this patent is extended or adjusted under 35 U.S.C. 154(b) by 319 days.

(21) Appl. No.: 17/159,402

(22) Filed: Jan. 27, 2021

(65) Prior Publication Data

US 2021/0146309 A1 May 20, 2021

Related U.S. Application Data

(63) Continuation of application No. PCT/JP2019/035434, filed on Sep. 10, 2019.

(30) Foreign Application Priority Data

Sep. 28, 2018 (JP) .................. 2018-183725

(51) Int. Cl.
*B01D 61/18* (2006.01)
*B01D 63/08* (2006.01)

(52) U.S. Cl.
CPC ............ *B01D 61/18* (2013.01); *B01D 63/08* (2013.01)

(58) Field of Classification Search
CPC ........ B01D 39/10; B01D 39/14; B01D 39/20; B01D 39/2027; B01D 39/2068; B01D 39/108; B01D 43/00; B01D 61/00; B01D 63/00; B01D 63/08; B01D 63/081; B01D 67/00; B01D 67/0039; B01D 67/0044; B01D 67/0076; B01D 67/0079;
(Continued)

(56) References Cited

U.S. PATENT DOCUMENTS

| 10,858,624 B2 | 12/2020 | Banju et al. |
| 2004/0029267 A1* | 2/2004 | Martin .................. C12M 27/16 435/292.1 |

(Continued)

FOREIGN PATENT DOCUMENTS

| JP | 2015188314 A | 11/2015 |
| JP | 6249124 B1 | 12/2017 |

(Continued)

OTHER PUBLICATIONS

International Search Report issued for PCT/JP2019/035434, dated Nov. 19, 2019.
(Continued)

*Primary Examiner* — Allison G Fitzsimmons
(74) *Attorney, Agent, or Firm* — ArentFox Schiff LLP

(57) ABSTRACT

A filtration filter having a filter substrate defining a plurality of through-holes extending from a first principal surface to a second principal surface opposite the first principal surface; and a pair of projections between adjacent through-holes of the plurality of through-holes, the pair of projections being on corresponding end portions on opposite sides in a width direction of the filter substrate and protruding from the first principal surface so as to define a reservoir part with the first principal surface.

9 Claims, 7 Drawing Sheets

(58) Field of Classification Search
CPC .............. B01D 67/0081; B01D 67/0093; B01D 69/00; B01D 69/06; B01D 69/10; B01D 69/108; B01D 71/00; B01D 71/02; B01D 71/022; B01D 71/028; B01D 2201/0415; B01D 2201/84; B01D 2257/91; B01D 2323/34; B01D 2323/345; B01D 2323/40; B01D 2325/00; B01D 2325/04; B01D 2325/06; B01D 2325/08
See application file for complete search history.

(56) References Cited

U.S. PATENT DOCUMENTS

| | | | |
|---|---|---|---|
| 2017/0198248 A1* | 7/2017 | Kinuta | .......... C12M 47/02 |
| 2018/0312803 A1 | 11/2018 | Banju et al. | |
| 2018/0353881 A1 | 12/2018 | Yamamoto et al. | |
| 2018/0362917 A1* | 12/2018 | Kondo | .......... B01D 39/20 |
| 2019/0120735 A1 | 4/2019 | Kinuta et al. | |
| 2019/0185804 A1 | 6/2019 | Banju et al. | |
| 2021/0047613 A1 | 2/2021 | Banju et al. | |

FOREIGN PATENT DOCUMENTS

| | | |
|---|---|---|
| KR | 20170032233 A | 3/2017 |
| WO | 2018020897 A1 | 2/2018 |
| WO | 2018116883 A1 | 6/2018 |
| WO | 2018163757 A1 | 9/2018 |

OTHER PUBLICATIONS

Written Opinion of the International Searching Authority issued for PCT/JP2019/035434, dated Nov. 19, 2019.

* cited by examiner

FILTRATION FILTER AND FILTRATION METHOD

CROSS REFERENCE TO RELATED APPLICATIONS

The present application is a continuation of International application No. PCT/JP2019/035434, filed Sep. 10, 2019, which claims priority to Japanese Patent Application No. 2018-183725, filed Sep. 28, 2018, the entire contents of each of which are incorporated herein by reference.

FIELD OF THE INVENTION

The present invention relates to a filtration filter that captures a filtration target contained in a liquid. The present invention also relates to a filtration method implemented with the filtration filter.

BACKGROUND OF THE INVENTION

An example of such a filtration filter known in the art includes the filtration filter disclosed in Patent Document 1. Patent Document 1 discloses a filtration filter that captures a filtration target, or more specifically, cells contained in a cell dispersion liquid.

Patent Document 1: Japanese Unexamined Patent Application Publication No. 2015-188314

SUMMARY OF THE INVENTION

Such a filtration filter known in the art has room for improvement in keeping the filtration target from drying out.

The present invention therefore has been made to solve the above-mentioned problem, and it is an object of the present invention to provide a filtration filter that helps keep a filtration target from drying out.

To attain the aforementioned objective, a filtration filter according to an aspect of the present invention has a filter substrate defining a plurality of through-holes extending from a first principal surface to a second principal surface opposite the first principal surface; and a pair of projections between adjacent through-holes of the plurality of through-holes, the pair of projections being on corresponding end portions on opposite sides in a width direction of the filter substrate and protruding from the first principal surface so as to define a reservoir part with the first principal surface. The filter substrate is a site on which a filtration target contained in a liquid is to be captured.

The present invention helps keep the filtration target from drying out.

DETAILED DESCRIPTION OF THE PREFERRED EMBODIMENTS

Figure 1:
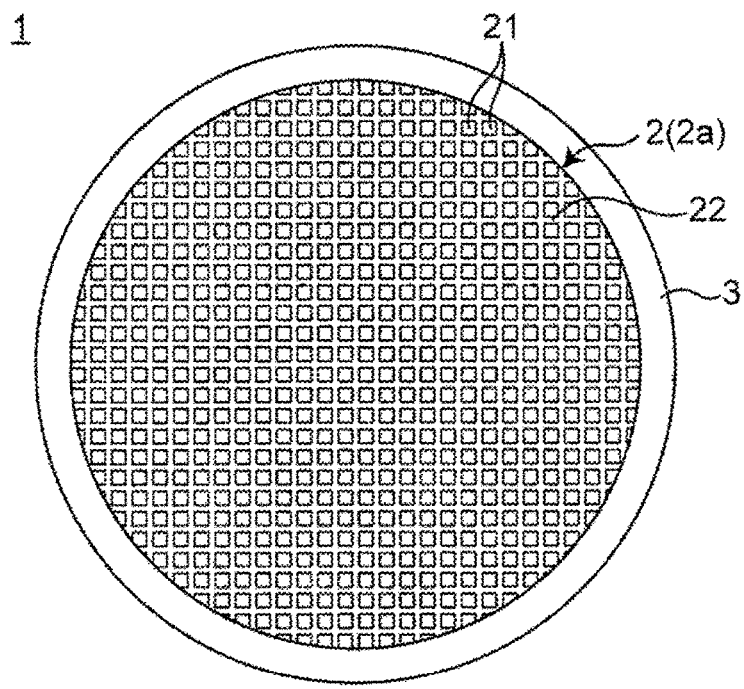
FIG. 1 is a plan view of a filtration filter according to an embodiment of the present invention.

The inventors in the present application conducted a thorough study regarding ways to keep a filtration target from drying out. The findings of this study are as follows.

When a liquid containing a filtration target is filtered through a filtration filter, the filtration target caught and left on the filtration filter is exposed to air. The filtration target may be cells or any other substance derived from living organisms. Such a substance is particularly prone to adhere to the filtration filter when drying out on exposure to air. This makes it difficult to collect the filtration target, and the filtration target may become less active.

After thorough study, the inventors found that a filtration target captured and immersed in a liquid retained in a reservoir part of a filtration filter was successfully kept from drying out. The reservoir part was provided on a principal surface of the filtration filter in a manner so as to retain some of the liquid. These findings resulted in the present invention, which will be described below.

A filtration filter according to an aspect of the present invention has a filter substrate defining a plurality of through-holes extending from a first principal surface to a second principal surface opposite the first principal surface; and a pair of projections between adjacent through-holes of the plurality of through-holes, the pair of projections being on corresponding end portions on opposite sides in a width direction of the filter substrate and protruding from the first principal surface so as to define a reservoir part with the first principal surface. The filter substrate is a site on which a filtration target contained in a liquid is to be captured.

That is, the reservoir part is provided on the filter substrate on which the filtration target is to be captured. The filtration target may thus be immersed in the liquid retained in the reservoir part and may be kept from drying out accordingly.

The pair of projections may each have an inner face defining the reservoir part, and the inner face of each projection may be inclined or curved in such a manner that a perimeter of the reservoir part increases with increasing distance from the first principal surface. This provides greater ease in retaining the liquid in the reservoir part.

The pair of projections may each have an outer face opposite the inner face, and the outer face of each projection may extend from the first principal surface and be inclined or curved toward the inside of the through-hole that is adjoined by the projection. This provides much greater ease in retaining the liquid in the reservoir part.

When a cross section of the filtration filter is taken in a direction from the first principal surface to the second principal surface and along a line passing through the adjacent through-holes, a straight line forming a connection between tops of inner faces of projections of the pair of projections may be longer than the second principal surface between the adjacent through-holes. This provides much greater ease in retaining the liquid in the reservoir part.

Each projection may form a loop that extends along a periphery of the through-hole that is adjoined by the projection. This provides much greater ease in retaining the liquid in the reservoir part.

When viewed in a plan view from the first principal surface, each of the projections may include a first linear section, a second linear section, and a corner section that connects an end portion of the first linear section and an end portion of the second linear section. The height of the corner section as measured from the first principal surface may be less than the height of the first linear section and may be less than the height of the second linear section. This enables a reduction in the stress that is exerted on the corner section when the filtration filter is bent and depressed in the thickness direction. The projections are less prone to damage accordingly.

The second principal surface may be flat. The filtration target may be immersed in the liquid retained in the reservoir part that is deliberately provided on such an intrinsically flat filter. The filtration targets are thus kept from drying out.

The filtration filter may comprise a porous metallic membrane for use in taking out, by filtration, a filtration target that is a substance derived from living organisms. The substance derived from living organisms can soon dry out on such a porous metallic membrane typically having high thermal conductivity. The substance derived from living organisms may be immersed in the liquid retained in the reservoir part that is deliberately provided on the porous metallic membrane included in the filtration filter. The substance derived from living organisms may thus be kept from drying out. This enables the substance derived from living organisms to survive over an extended period of time while observations are being conducted.

The distance between the first principal surface and a crest of each of the projections is preferably not less than 10 nm and not more than 10 times the thickness of the filter substrate. The filtration target, or more specifically, a substance derived from living organisms may thus be kept from drying out. This enables an increase in the ratio of the substance collected alive.

A filtration method according to another aspect of the present invention includes pouring a liquid containing the filtration target over the first principal surface of the filtration filter according to the aspect above so as to capture some of the liquid, together with the filtration target, in the reservoir part.

That is, the liquid containing the filtration target is poured over the first principal surface of the filtration filter. Together with the filtration target, some of the liquid is consequently captured in the reservoir part. The filtration target may thus be immersed in the liquid retained in the reservoir part and may be kept from drying out accordingly.

Hereinafter, an embodiment of the present invention will be described with reference to the accompanying drawings. Elements in the drawings are exaggerated for easy-to-understand illustration.

Embodiment

Figure 2:
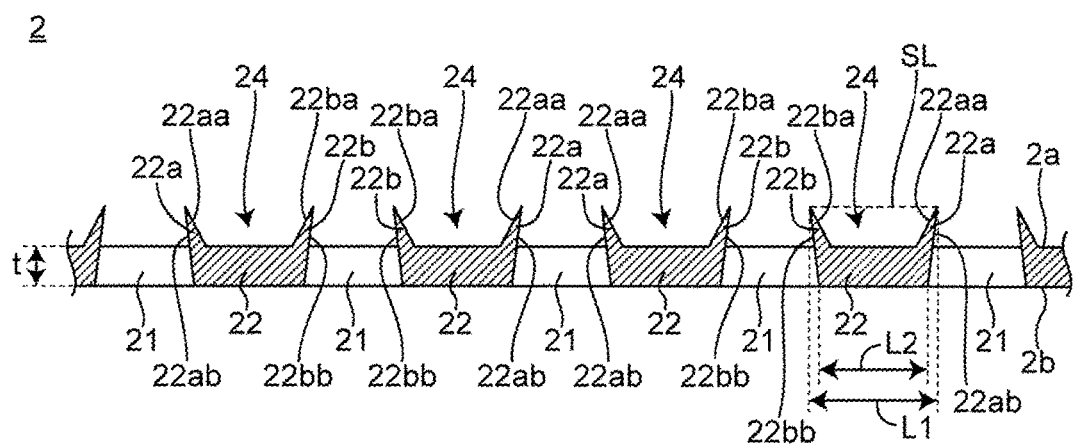
FIG. 2 is an enlarged sectional view of part of the filtration filter in FIG. 1.

The following describes a configuration of a filtration filter according to the present embodiment. FIG. 1 is a plan view of a filtration filter according to an embodiment of the present invention. FIG. 2 is an enlarged sectional view of part of the filtration filter in FIG. 1.

As illustrated in FIG. 1, a filtration filter 1 according to the present embodiment includes a filter portion 2 and a frame portion 3. The filter portion 2 captures filtration targets contained in a liquid. The frame portion 3 annularly extends along the periphery of the filter portion 2 in a manner so as to surround the filter portion 2.

In the present embodiment, the term "filtration target" herein refers to matter that is contained in liquid and is to be taken out by filtration. The filtration target contained in the liquid may be a substance derived from living organisms such as cells (eukaryotes), bacteria (eubacteria), and viruses. Examples of cells (eukaryotes) include induced pluripotent stem cells (iPSCs), ES cells, stem cells, mesenchymal stem cells, mononuclear cells, single cells, cell clusters, floating cells, adherent cells, nerve cells, leukocytes, cells for regenerative medicine, autologous cells, cancer cells, circulating tumor cells (CTCs), HL-60 cells, HeLa cells, and fungi. Examples of bacteria (eubacteria) include *Escherichia coli* and *Mycobacterium tuberculosis.*

As illustrated in FIG. 2, the filter portion 2 is a sheet-like or membranous structure having a first principal surface 2a and a second principal surface 2b, which is opposite the first principal surface 2a. The filter portion 2 in the present embodiment is a porous metallic membrane for use in taking out, by filtration, a filtration target, or more specifically, a substance derived from living organisms. The filter portion 2 has through-holes 21, which extend from the first principal surface 2a to the second principal surface 2b. The filter portion 2 includes a filter substrate 22, which defines the through-holes 21. When a liquid containing filtration targets is poured over the first principal surface 2a, the filtration targets contained in the liquid are captured on the filter substrate 22, and the liquid flows through the through-holes 21 to pass through the filter portion 2.

The filter portion 2 is, for example, circular, rectangular, or elliptic when viewed in the thickness direction of the filtration filter 1. Referring to FIG. 1, the filter portion 2 in the present embodiment is substantially circular. The expression "substantially circular" herein means that the ratio between the length of the major axis is not less than 1.0 times and not more than 1.2 times the length of the minor axis. The frame portion 3 holds the periphery of the filter portion 2 to increase the mechanical strength of the filter portion 2. The frame portion 3 is optional.

The through-holes 21 are arranged in a periodic array on the first principal surface 2a and the second principal surface 2b of the filter portion 2. The through-holes 21 of the filter portion 2 in the present embodiment are provided at regular intervals and arranged in a matrix.

The through-holes 21 in the present embodiment are square when viewed from the first principal surface 2a of the filter portion 2. The shape of each through-hole 21 is not limited to a square and may be, for example, a rectangle, a circle, or an ellipse.

Referring to FIG. 2, the through-holes 21 in the present embodiment each have a trapezoidal shape when viewed in cross section taken in the thickness direction of the filter portion 2. Specifically, when viewed in cross section, each through-hole 21 has a shape with four sides, only two of which, namely, a short side (i.e., a short base) on the first principal surface 2a and a long side (i.e., a long base) on the second principal surface 2b are parallel. The angle which lateral sides (i.e., legs) of the trapezoidal shape each form with the second principal surface 2b is, for example 80°. The shape of each through-hole 21 viewed in cross section is not limited to a trapezoid and may be, for example, a rectangle. The shape of each through-hole 21 viewed in cross section may be symmetrical or asymmetrical.

The through-holes 21 in the present embodiment are provided at regular intervals in two array directions parallel to the respective sides of the square viewed from the first principal surface 2a of the filter portion 2. That is, the through-holes 21 are arranged in a square grid array. Owing to the through-holes 21 arranged in a square grid array, the filtration filter 1 achieves a high aperture ratio, and the resistance to the flow of liquid through the filtration filter 1 may be reduced accordingly. This enables a shortening of filtration time, and consequently, the stress on the filtration targets may be lightened.

Instead of being arranged in a square grid array, the through-holes 21 may be arranged in a quasi-periodic array or in a periodic array. The periodic array may be any quadrate array, examples of which include a rectangular array with intervals in one array direction not coinciding with intervals in the other array direction. Alternatively, the through-holes 21 may be arranged in a triangular grid array or in a regular triangle grid array. It is required that the filter portion 2 have more than one through-hole 21. The arrangement of the through-holes 21 is not limited to a particular pattern.

The intervals between the through-holes 21 are determined as appropriate according to the type (i.e., size, form, properties, or elasticity) or the volume of the filtration targets. The intervals between the through-holes 21 refers to a center-to-center distance of adjacent ones of the through-holes 21 viewed from the first principal surface 2a of the filter portion 2. When the structure includes a periodic array of through-holes 21, the interval between the through-holes 21 is, for example, more than the length of each side of each through-hole 21 and not more than 10 times the length of each side, and is preferably not more than three times the length of each side of each through-hole 21. The aperture ratio of the filter portion 2 is, for example, not less than 10% and is preferably not less than 25%. The resistance to the flow of liquid through the filter portion 2 may thus be reduced. This enables a shortening of filtration time, and consequently, the stress on the filtration targets may be lightened. Dividing the area of the through-holes 21 by the projected area of a hypothetical example of the first principal surface 2a with no through-hole 21 gives the aperture ratio.

The thickness of the filter portion 2, namely, t is preferably more than 0.1 times and not more than 100 times the dimension of each through-hole 21. The thickness of the filter portion 2, namely, t is more preferably more than 0.5 times and not more than 10 times the dimension of each through-hole 21. The resistance imparted by the filtration filter 1 to the flow of liquid may thus be reduced, and a shortening of filtration time may be achieved accordingly. Consequently, the stress on the filtration targets may be lightened.

The first principal surface 2a of the filter portion 2 may come into contact with the liquid containing the filtration targets. It is thus preferred that the first principal surface 2a have a small surface roughness. The term "surface roughness" herein refers to the mean value of the difference between the maximum value and the minimum value as determined by a stylus profilometer at freely selected five spots on the first principal surface 2a. In the present embodiment, the surface roughness is preferably smaller than the size of each filtration target and is more preferably smaller than half the size of the filtration target. Specifically, the through-holes 21 on the first principal surface 2a of the filter portion 2 are apertures in the same plane. The filter substrate 22, which is the filter portion 2 except for the through-holes 21, is continuous and is formed as one member. This enables a reduction in the volume of filtration targets that get deposited on the first principal surface 2a of the filter portion 2, and the resistance to the flow of liquid may be reduced accordingly.

The material of the filter substrate 22 is made mainly of a metal or a metal oxide. Constituents of the filter substrate 22 may be gold, silver, copper, platinum, nickel, palladium, titanium, alloy of these metals, and oxides of these metals.

Figure 3:
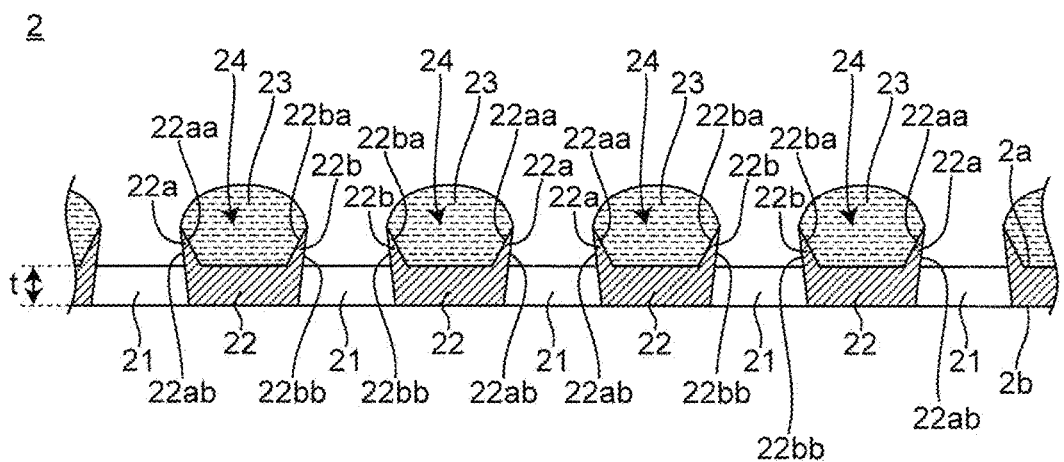
FIG. 3 is an enlarged sectional view of part of the filtration filter in FIG. 1, illustrating a state in which a liquid is captured in a reservoir part.

Referring to FIG. 2, which is a sectional view of the filtration filter taken in the direction from the first principal surface 2a to the second principal surface 2b (i.e., in the thickness direction of the filter portion 2) and along a line passing through adjacent ones of the through-holes 21, the filter substrate 22 between two adjacent ones of the through-holes 21 has a pair of projections, namely, a projection 22a and a projection 22b, which are provided on corresponding end portions of opposite sides in the width direction of the filter substrate 22 and protrude from the first principal surface 2a. As illustrated in FIG. 3, the first principal surface 2a and the pair of projections (i.e., the projections 22a and 22b) of the filter substrate 22 in the present embodiment define a reservoir part 24. Some of a liquid 23, which contains filtration targets, is to be retained in the reservoir part 24. That is, the reservoir part 24 is provided on the filter substrate 22 on which filtration targets are to be captured. The filtration targets may be immersed in the liquid 23 retained in the reservoir part 24 and may thus be kept from drying out.

The projection 22a has an inner face 22aa, and the projection 22b has an inner face 22ba. The inner faces 22aa and 22ba define the reservoir part 24 and are inclined or curved in such a manner that the perimeter of the reservoir part 24 increases with increasing distance from the first principal surface 2a. The liquid 23 can be readily captured in the reservoir part 24 accordingly. This provides greater ease in retaining the liquid 23.

Referring to FIG. 2, which is a sectional view of the filtration filter taken in the direction from the first principal surface 2a to the second principal surface 2b and along a line passing through adjacent ones of the through-holes 21, L1 in the present embodiment is greater than L2, where L1 denotes the length of a straight line SL forming a connection between the tops of the inner faces of the pair of projections (i.e., the length of the straight line SL connecting the top of the inner face 22aa of the projection 22a to the top of the inner face 22ba of the projection 22b), and L2 denotes the length of the second principal surface 2b in the width direction. The reservoir part 24 thus has a wide opening on the side from which the liquid 23 containing filtration targets is poured. The surface tension of the liquid 23 is increased correspondingly. This provides much greater ease in retaining the liquid 23 in the reservoir part 24.

The projection 22a has an outer face 22ab opposite the inner face 22aa defining the reservoir part 24. The outer face 22ab of the projection 22a in the present embodiment extends from the first principal surface 2a in a manner so as to be inclined or curved toward the inside of the through-hole 21 adjoined by the projection 22a. Similarly, the projection 22b has an outer face 22bb opposite the inner face 22ba defining the reservoir part 24. The outer face 22bb of the projection 22b in the present embodiment extends from the first principal surface 2a in a manner so as to be inclined or curved toward the inside of the through-hole 21 adjoined by the projection 22b. The reservoir part 24 thus has a wide opening on the side from which the liquid 23 containing filtration targets is poured. The surface tension of the liquid 23 is increased correspondingly. This provides much greater ease in retaining the liquid 23 in the reservoir part 24.

Figure 4:
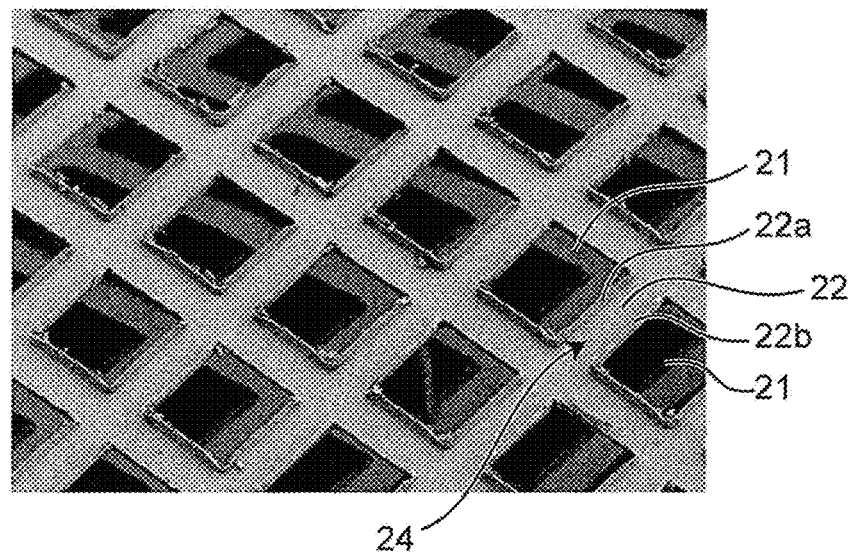
FIG. 4 is an enlarged perspective view of a filter portion, illustrating a region of the filter portion viewed from a first principal surface side.
Figure 5:
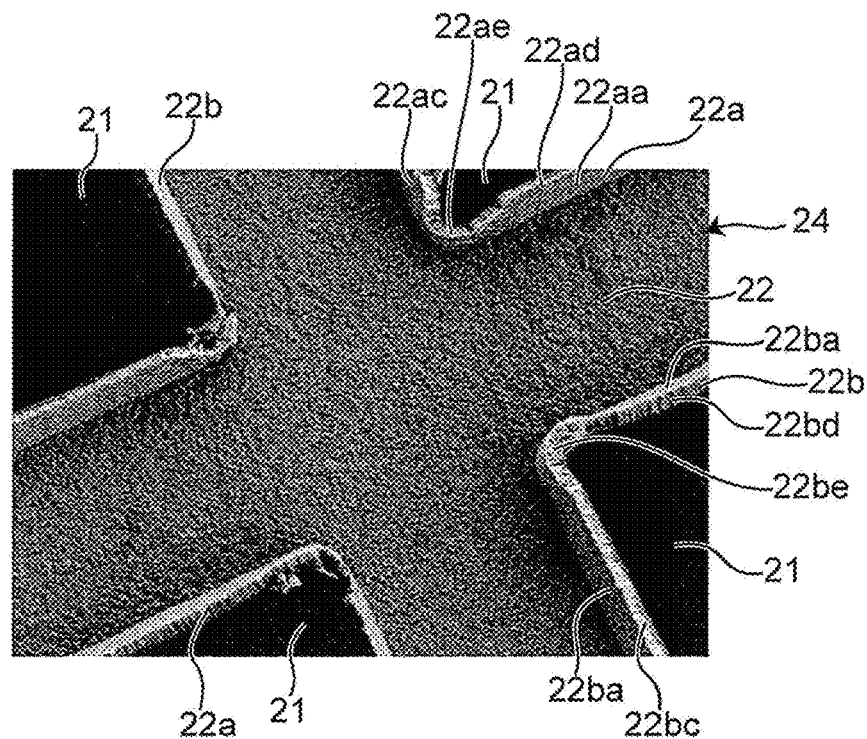
FIG. 5 is a close-up perspective view of part of the region in FIG. 4.

FIG. 4 is an enlarged perspective view of the filter portion 2, illustrating a region of the filter portion 2 viewed from the first principal surface 2a side. FIG. 5 is a close-up perspective view of part of the region in FIG. 4.

As illustrated in FIGS. 4 and 5, each projection 22a forms a loop in a manner so as to extend along the periphery of the through-hole 21 adjoined by the projection 22a. Similarly, each projection 22b forms a loop in a manner so as to extend along the periphery of the through-hole 21 adjoined by the projection 22b. The liquid 23 retained in the reservoir part 24 is thus kept from leaking through the through-holes 21. This provides much greater ease in retaining the liquid in the reservoir part 24.

When viewed in a plan view from the first principal surface 2a, each projection 22a includes a first linear section 22ac, a second linear section 22ad, and a corner section 22ae, which forms a connection between an end portion of the first linear section 22ac and an end portion of the second linear section 22ad. The height of the corner section 22ae as measured from the first principal surface 2a is less than the height of the first linear section 22ac and is less than the height of the second linear section 22ad. In other words, the edge line of the crest of the first linear section 22ac and the edge line of the crest of the second linear section 22ad bow downward at the corner section 22ae. This enables a reduction in the stress that is exerted on the corner section 22ae when the filtration filter 1 is bent and depressed in the thickness direction. The projections 22a are less prone to damage accordingly.

The same holds true for the projections 22b. When viewed in plan, each projection 22b includes a first linear section 22bc, a second linear section 22bd, and a corner section 22be, which forms a connection between an end portion of the first linear section 22bc and an end portion of the second linear section 22bd. The height of the corner section 22be as measured from the first principal surface 2a is less than the height of the first linear section 2bc and is less than the height of the second linear section 22bd. This enables a reduction in the stress that is exerted on the corner section 22be when the filtration filter 1 is bent and depressed in the thickness direction. The projections 22b are less prone to damage accordingly.

Figure 6:
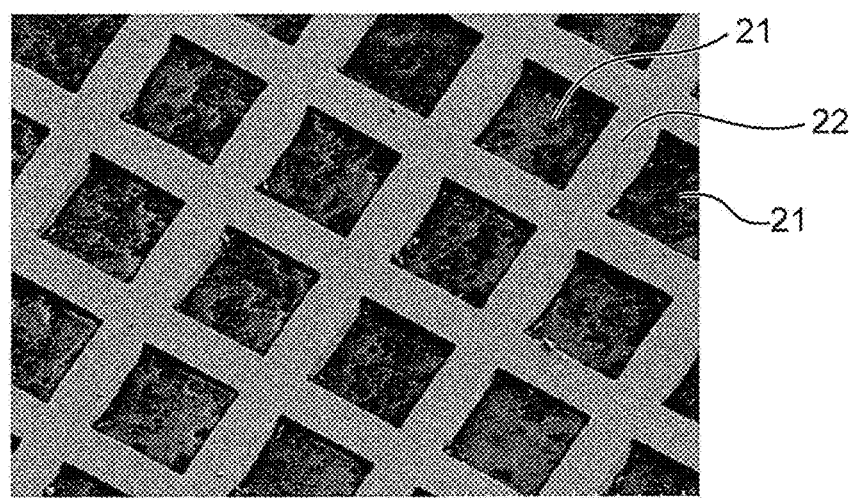
FIG. 6 is an enlarged perspective view of the filter portion, illustrating a region of the filter portion viewed from a second principal surface side.
Figure 7:
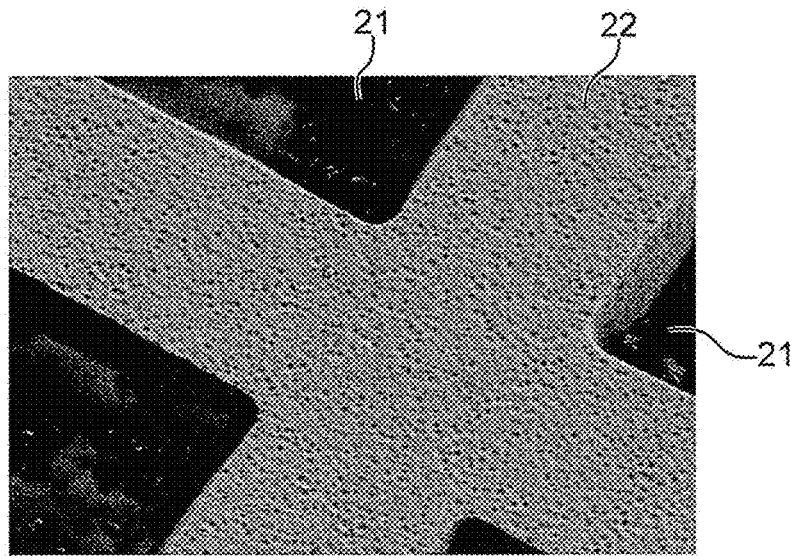
FIG. 7 is a close-up perspective view of part of the region in FIG. 6.

FIG. 6 is an enlarged perspective view of the filter portion 2, illustrating a region of the filter portion 2 viewed from the second principal surface 2b side. FIG. 7 is a close-up perspective view of part of the region in FIG. 6.

In the present embodiment, an intrinsically flat filter having two principal surfaces is processed such that the reservoir part 24 is deliberately formed on one of the principal surfaces. Consequently, the second principal surface 2b of the filter portion 2 is flat as in FIGS. 6 and 7. That is, the second principal surface 2b of the filter portion 2 is entirely in contact with a level surface on which the filter portion 2 is mounted. The filtration targets may be immersed in the liquid 23 retained in the reservoir part 24 that is deliberately provided on the intrinsically flat filter. The filtration targets are thus kept from drying out.

As mentioned above, the filter portion 2 in the present embodiment is a porous metallic membrane for use in taking out, by filtration, filtration targets, or more specifically, a substance derived from living organisms. The porous metallic membrane is an intrinsically flat filter having two principal surfaces. The substance derived from living organisms can soon dry out on such a porous metallic membrane typically having high thermal conductivity. As a workaround, the reservoir part 24 is deliberately provided on the filter portion 2 in the present embodiment. The reservoir part 24 may be provided on a porous metallic membrane included in the filtration filter 1 such that a substance derived from living organisms is immersed in the liquid retained in the reservoir part 24. The substance derived from living organisms may thus be kept from drying out. This enables the substance derived from living organisms to survive over an extended period of time while observations are being conducted.

The porous metallic membrane can yield improvements over porous resin membranes in terms of accuracy of dimensions and layout of through-holes formed therein. The filter portion 2 made of a porous metallic membrane enables an increase in the collection rate of filtration targets accordingly. Filtration targets adhering to a porous metallic membrane can be peeled off more easily than filtration targets adhering to a porous resin membrane. Thus, the filtration targets adhering to the porous metallic membrane are less likely to become damaged when being peeled off.

The following describes a filtration method implemented with the filtration filter 1 according to the present embodiment.

First, the filtration filter 1 described above with reference to FIGS. 1 to 7 is prepared.

Subsequently, a liquid containing filtration targets is poured over the first principal surface 2a. Together with the filtration targets, some of the liquid 23 is consequently captured in the reservoir part 24 as in FIG. 3. The remainder of the liquid 23 that has escaped being captured in the reservoir part 24 flows through the through-holes 21 to pass through the filter portion 2.

The filtration targets captured in the reservoir part 24 are consequently immersed in the liquid 23. In this way, the filtration targets are kept from drying out.

The following describes an example of a method for producing the filter portion 2 of the filtration filter 1 according to the present embodiment. FIGS. 8A to 8G are sectional views, schematically illustrating an example of the method for producing the filter portion 2 of the filtration filter 1 according to the present embodiment. FIG. 9 is an enlarged sectional view of the region surrounded by a dotted line in FIG. 8E.

Figure 8A:
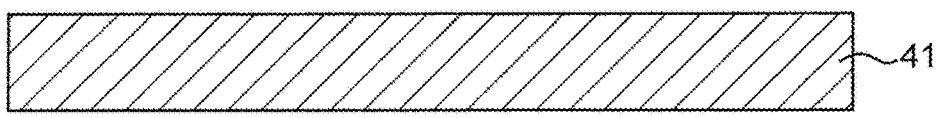
FIG. 8A is a sectional view, schematically illustrating an example of a method for producing the filter portion of the filtration filter in FIG. 1.
Figure 9:
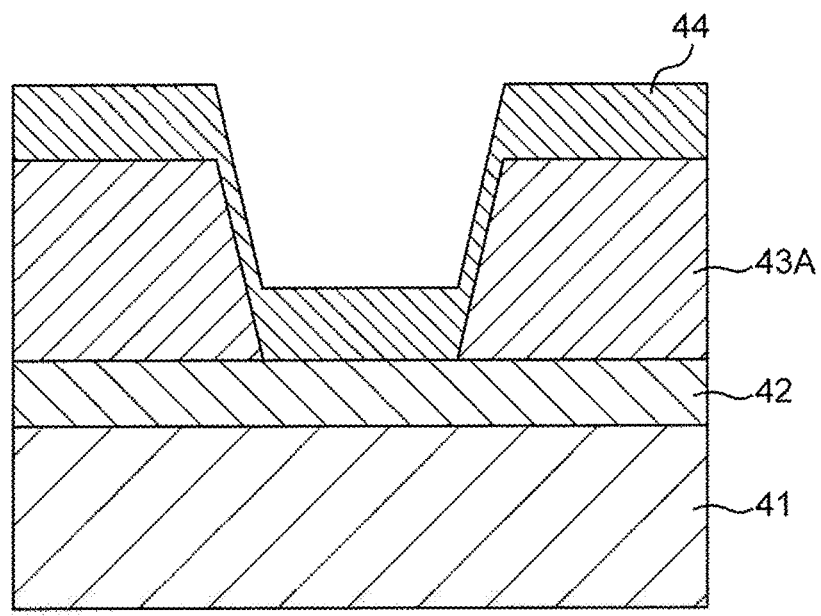
FIG. 9 is an enlarged sectional view of a region surrounded by a dotted line in FIG. 8E.

Referring to FIG. 8A, a substrate 41 is prepared.

Figure 8B:
FIG. 8B is a sectional view, illustrating a step that is to be performed subsequent to the step in FIG. 8A.

Referring to FIG. 8B, the substrate 41 is then overlaid with a sputter-deposited film 42.

Figure 8C:
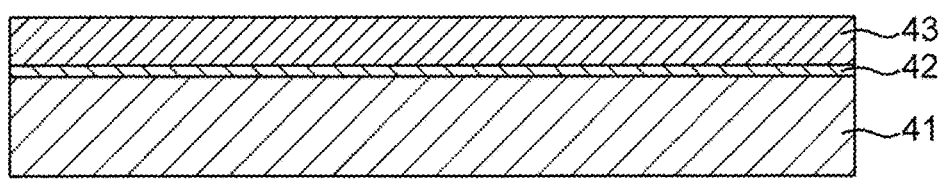
FIG. 8C is a sectional view, illustrating a step that is to be performed subsequent to the step in FIG. 8B.

Referring to FIG. 8C, the sputter-deposited film 42 is then overlaid with a photoresist film 43.

Figure 8D:
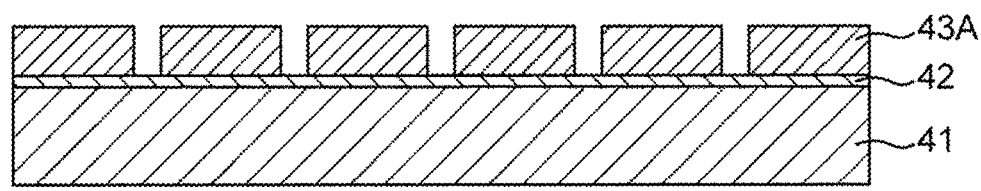
FIG. 8D is a sectional view, illustrating a step that is to be performed subsequent to the step in FIG. 8C.

Referring to FIG. 8D, the photoresist film 43 is exposed to radiation and undergoes a development process, in which a region corresponding to a filter substrate 22 is removed. Consequently, a photoresist image 43A is produced. As illustrated in FIG. 9, the photoresist image 43A is shaped in such a manner that the region corresponding to the filter substrate 22 is tapered, that is, the perimeter of the region increases gradually with increasing distance from the sputter-deposited film 42.

Figure 8E:
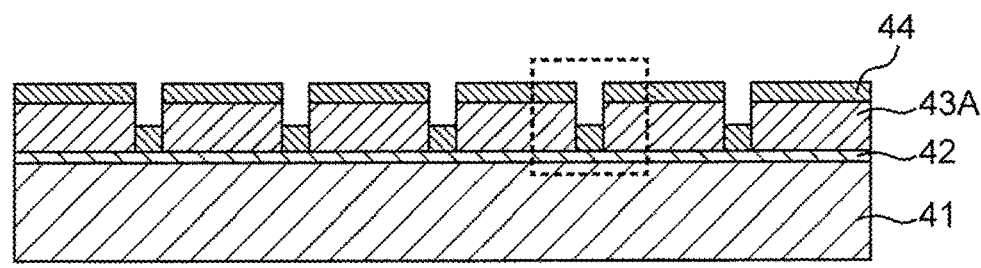
FIG. 8E is a sectional view, illustrating a step that is to be performed subsequent to the step in FIG. 8D.

Referring to FIG. 8E, a metal 44 is then evaporatively deposited from above the photoresist image 43A.

Figure 8F:
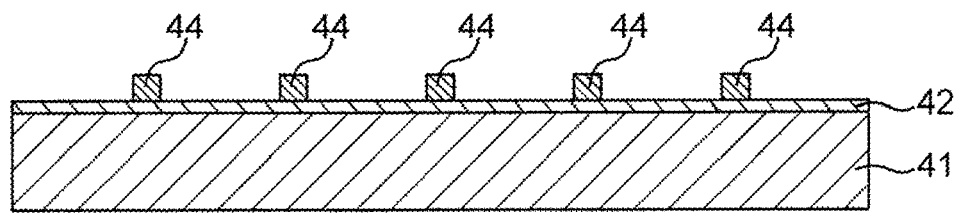
FIG. 8F is a sectional view, illustrating a step that is to be performed subsequent to the step in FIG. 8E.

Referring to FIG. 8F, the photoresist image 43A and the metal 44 deposited on the photoresist image 43A are dissolved and peeled off, leaving behind some of the metal 44 on the sputter-deposited film 42. The metal 44 left on the sputter-deposited film 42 is to be used as the filter substrate 22.

Figure 8G:
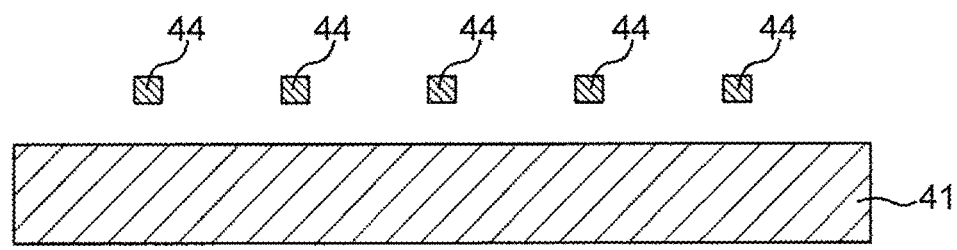
FIG. 8G is a sectional view, illustrating a step that is to be performed subsequent to the step in FIG. 8F.

Referring to FIG. 8G, the sputter-deposited film 42 on the substrate 41 is etched and removed to separate, from the substrate 41, the metal 44 for use as the filter substrate 22. The filter portion 2 of the filtration filter 1 is obtained accordingly.

EXAMPLES

The following describes a method for producing the filter portion 2 of the filtration filter 1 according to an example.

A silicon substrate cleaned by surface washing was prepared as the substrate 41 in FIG. 8A.

As in FIG. 8B, two layers, or more specifically, a titanium film and a copper film were formed as the sputter-deposited film 42 on the substrate 41. Titanium was deposited with a thickness of 50 nm. Copper was deposited with a thickness of 500 nm.

The sputter-deposited film 42 was then coated with a positive-type liquid photoresist, which was deposited by using a spin coater and was then dried by baking on a hot plate. Consequently, the photoresist film 43 was formed as in FIG. 8C. The spin coater ran for 30 seconds at a rotation speed of 1,140 rpm. As a positive-type liquid photoresist, PFI-37A (manufactured by Sumitomo Chemical Co., Ltd.) was used. The hot plate was operated for 90 seconds at 90° C. Under the conditions mentioned above, the photoresist film 43 was formed with a thickness of 2.0 µm on the sputter-deposited film 42.

The photoresist film 43 was exposed to radiation by using lithography equipment, or more specifically an i-line stepper and was developed by using a developing machine, or more specifically puddle development equipment. Consequently, the photoresist image 43A was formed as in FIG. 8D. A developer, or more specifically, tetramethyl ammonium hydroxide (TMAH) was used in this process, which was followed by water-washing and a drying process.

When the exposure dose provided by the lithography equipment was not less than 2,200 J/cm$^2$ and not more than 2,450 J/cm$^2$, each region being part of the photoresist image 43A and corresponding to the filter substrate 22 was tapered as desired (i.e., as in FIG. 9, or more specifically, at an inclination of, for example, 10°). When the exposure dose provided by the lithography equipment was not less than 2,500 J/cm$^2$ and not more than 3,300 J/cm$^2$, each region being part of the photoresist image 43A and corresponding to the filter substrate 22 was not satisfactorily tapered. The reason for this was probably as follows: with increasing exposure dose to the photoresist film 43, the penetration depth of the emitted beam increased, making it difficult to form a gradient in the thickness direction of the photoresist film 43.

When the distance from the focal point given by the lithography equipment was not less than +0.5 µm and not more than +2.0 µm, each region being part of the photoresist image 43A and corresponding to the filter substrate 22 was tapered as desired (i.e., as in FIG. 9, or more specifically, at an inclination of, for example, 10°). When the distance from the focal point given by the lithography equipment was not less than −0.5 µm and not more than 0.0 µm, each region being part of the photoresist image 43A and corresponding to the filter substrate 22 was not satisfactorily tapered. The reason for this was probably as follows: with increasing proximity of the photoresist film 43 to the focal point, the penetration depth of the emitted beam increased, making it difficult to form a gradient in the thickness direction of the photoresist film 43.

The metal 44, or more specifically, titanium was then evaporatively deposited from above the photoresist image 43A as in FIG. 8E. Rotating the substrate 41 about its center while holding the substrate 41 at an inclination of 30° from a horizontal plane was conducive to efficient and uniform vapor deposition of titanium on inclined faces defining the tapered portions of the photoresist image 43A. Titanium was evaporatively deposited with a thickness of 0.5 µm under ambient substrate temperature conditions by using an evaporation apparatus, or more specifically, a vacuum evaporator manufactured by JEOL Ltd. The deposition rate was 5 Å/sec. The rotation speed of the substrate 41 was not less than 5 rpm and not more than 40 rpm. More specifically, the substrate 41 was rotated at a speed of 30 rpm. The film deposition was completed in 16.7 minutes.

When the substrate 41 was held parallel to a horizontal plane and was not rotated during deposition, titanium slid over the inclined faces defining the tapered portions of the photoresist image 43A, thus making it difficult to achieve efficient and uniform vapor deposition of titanium on the inclined faces. Titanium deposited on the corner sections 22*ae* and 22*be*, each of which formed a connection between two adjacent ones of the inclined faces defining the tapered portions of the photoresist image 43A, was more prone to sliding down the surface than titanium deposited on any other section, and the layer formed on the sputter-deposited film 42 and corresponding to the corner sections 22*ae* and 22*be* was brought down in profile accordingly.

A lift-off system capable of high-pressure spraying and a photoresist stripper, or more specifically, N-methyl-2-pyrrolidone (NMP) were used to peel off, as in FIG. 8F, the photoresist image 43A and the metal 44 evaporatively deposited on the photoresist image 43A. Isopropyl alcohol (IPA) was used in the subsequent cleaning process, which was followed by water-washing and drying.

Subsequently, an immersion process was performed in an etchant agitated by a stirrer, and etching was performed to remove copper from the sputter-deposited film 42. Consequently, the metal 44 for use as the filter substrate 22 was separated from the substrate 41 as in FIG. 8G. As an etchant, a peracetic acid solution (a mixture of acetic acid, hydrogen peroxide, and water in a 5:5:90 ratio) was used. The immersion process was completed in 12 hours.

The filter portion 2 of the filtration filter 1 according to the example was obtained accordingly. The outside shape of each through-hole 21 on the second principal surface 2*b* side was a square of side 10 µm. The length L2 of the second principal surface 2*b* of the filter substrate 22 in the width direction was 4 µm. The thickness of the filter portion 2 (the distance between the first principal surface 2a and the second principal surface 2b) was 0.5 μm.

The filter portion 2 of the filtration filter 1 according to the example above was examined under an electron microscope, and the following describes results of observations.

Figure 10:
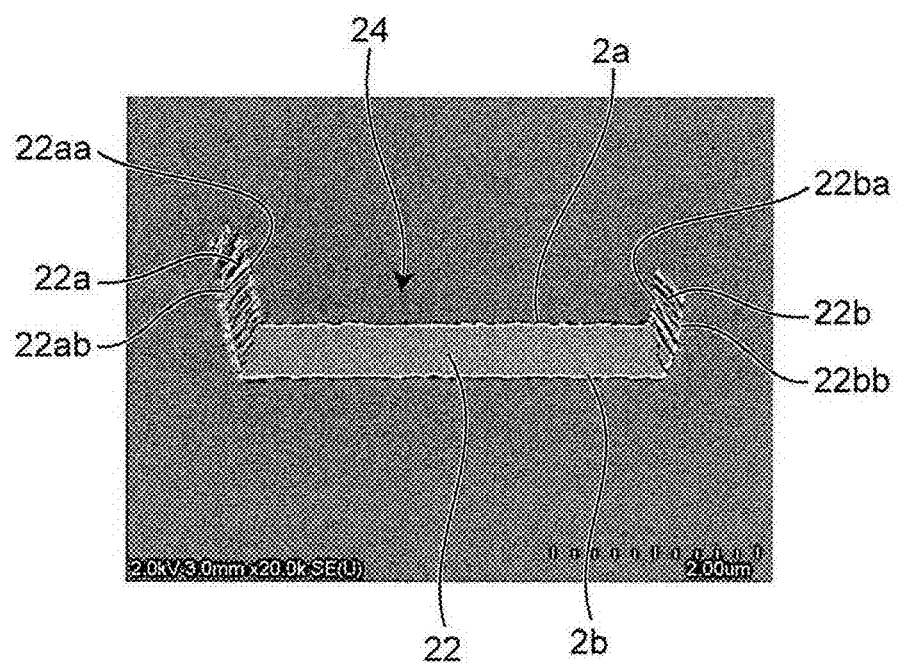
FIG. 10 is an enlarged sectional view of part of a filter portion of a filtration filter according to an example of the present invention.
Figure 11:
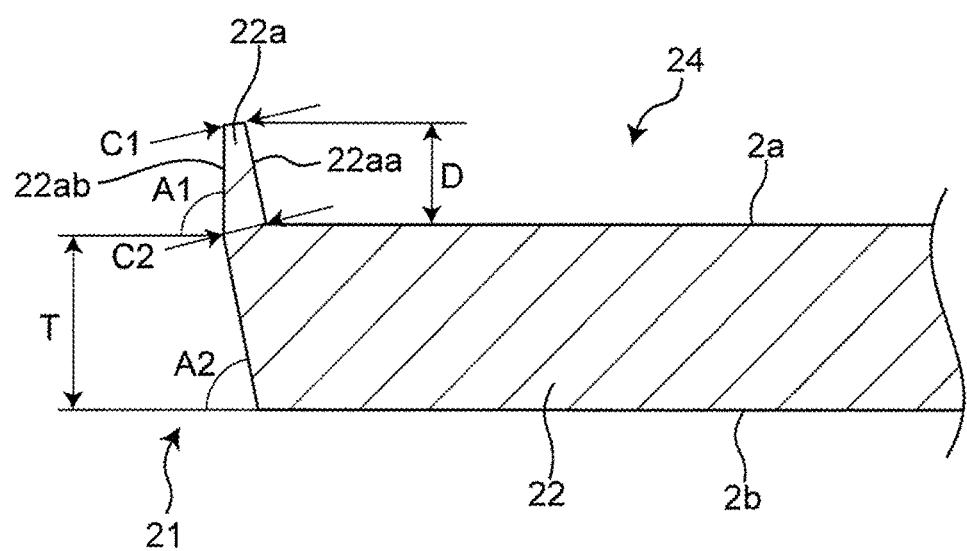
FIG. 11 is an enlarged sectional view of part of the filter portion of the filtration filter according to the example of the present invention, schematically illustrating relevant angles and dimensions.

Referring to FIG. 10, the filter portion 2 of the filtration filter 1 according to the example above was examined under an electron microscope, and it was found that the shape of each projection 22a and the shape of the corresponding projection 22b were not mirror images of each other in some places. Measurements were made on freely selected six points in the filter portion 2 to determine the angles and dimensions indicated in FIG. 11. Table 1 shows results of the measurements. The row headers in Table 1 are as follows. A1 denotes the angle which the outer face 22ab of the projection 22a forms with the first principal surface 2a. A2 denotes the inclination of the through-hole 21 from the first principal surface 2a. C1 denotes the distance between the top of the inner face 22aa of the projection 22a and the top of the outer face 22ab of the projection 22a. C2 denotes the distance between the proximal end of the inner face 22aa of the projection 22a and the proximal end of the outer face 22ab of the projection 22a. D denotes the height of the projection 22a, that is, the distance between the first principal surface 2a and the crest of the projection 22a. T denotes the thickness of the filter portion 2, that is, the thickness of the filter substrate 22.

TABLE 1

| | Measurements | | | | | |
|---|---|---|---|---|---|---|
| | 1 | 2 | 3 | 4 | 5 | 6 |
| A1 (°) | 85.62 | 82.45 | 87.78 | 84.23 | 86.47 | 82.38 |
| A2 (°) | 79.13 | 75.84 | 85.45 | 78.40 | 81.21 | 79.93 |
| C1 (nm) | 302 | 298 | 292 | 286 | 330 | 282 |
| C2 (nm) | 330 | 365 | 349 | 333 | 385 | 333 |
| D (nm) | 1,000 | 595 | 595 | 655 | 337 | 635 |
| T (nm) | 510 | 510 | 520 | 520 | 500 | 500 |

Whatever the relation between D and T may be, A1 is less than 90°, A2 is smaller than A1, and C1 is smaller than C2, as can be seen from Table 1.

Filtration filters were produced in Examples 1 to 8 and Comparative Example 1, and filtration was conducted to take out filtration targets (i.e., a substance derived from living organisms, or more specifically, cells) by using the respective filtration filters. The difference between these filtration filters are in the thickness T of the filter portion 2 and the height D of the projection 22a. Table 2 shows results obtained through the use of the filtration filters, each of which was experimentally used to filter two milliliters of a cell suspension containing $1 \times 10^6$ cells.

TABLE 2

| | Example 1 | Example 2 | Example 3 | Example 4 | Example 5 | Example 6 | Example 7 | Example 8 | Comparative Example |
|---|---|---|---|---|---|---|---|---|---|
| Height D of Projections (nm) | 10 | 100 | 1000 | 5000 | 10 | 5500 | 6000 | 5000 | 0 |
| Thickness T of Filter Portion (nm) | 500 | 500 | 500 | 500 | 550 | 550 | 500 | 450 | 500 |
| Cell Capture Rate (Number of Cells Remaining/Number of Introduced Cells) | 7% | 8% | 10% | 10% | 7% | 11% | 7% | 6% | 5% |
| Overall Collection Rate of Cells Collected about 3 Minutes Later | 90% | 70% | 40% | 30% | 90% | 30% | 10-30% | 10-20% | 93% |
| Survival Rate of Cells Collected about 3 Minutes Later | 30% | 60% | 75% | 90% | 30% | 90% | 10-50% | 10-40% | 0% |
| Living Cell Collection Rate | 27% | 42% | 30% | 27% | 27% | 27% | 1-15% | 1-8% | 0% |

The row headers in Table 2 are as follows. The cell capture rate is the ratio of the number of cells remaining in the filter portion of each filtration filter to the number of cells introduced into the filtration filter concerned (i.e., the number of cells remaining/the number of introduced cells). The overall collection rate of cells collected about three minutes later is the ratio of the number of cells washed with phosphate buffered saline (PBS) and collected from the filter portion after three minutes elapsed since the cells were introduced, to the number of cells remaining in the filter portion. The survival rate of cells collected about three minutes later is the ratio of the number of cells collected alive to the total number of cells collected from the filter portion. The living cell collection rate is the ratio of the number of cells collected alive from the filter portion to the number of cells remaining in the filter portion.

As can be seen from Table 2, the living cell collection rate was not less than 1% in each of the filtration filters of Examples 1 to 8, where the height D of the projections was not less than 10 nm. The living cell collection rate was 0% in the filtration filter of Comparative Example, where the height D of the projections was 0 nm. It was accordingly confirmed that projections the height (D) of which was not less than 10 nm helped keep cells from drying out and enabled an increase in the living cell collection rate, that is, an increase in the ratio of cells collected alive.

As can be seen from Table 2, the living cell collection rate was not less than 27% in each of the filtration filters of Examples 1 to 6, where the height D of the projections was not more than 10 times the thickness T of the filter portion. The living cell collection rate varied over a range of 1 to 15% in the filtration filters of Examples 7 and 8, where the height D of the projections was more than 10 times the thickness T of the filter portion. This was probably due to faulty sections in projections of the filtration filters of Examples 7 and 8, where the ratio of the height D of the projections to the thickness T of the filter portion was so high that it was difficult to ensure consistency and uniformity in the height D of the projections. It was accordingly confirmed that projections the height (D) of which was not more than 10 times the thickness T of the filter portion helped keep cells from drying out and enabled an increase in the living cell collection rate, that is, an increase in the ratio of cells collected alive.

The present invention is not limited to the embodiment above and may be implemented in various forms. The embodiment above describes that the filter portion 2 is a porous metallic membrane. In some embodiments, however, the filter portion 2 may be any other membrane filter or any other filter for use in taking out, by filtration, filtration targets contained in a liquid. Using, as the filter portion 2, a porous membrane made of a low-thermal-conductivity material such as silicon or resin will help minimize the evaporation of the liquid 23 retained in the reservoir part 24. This will enhance the effect of keeping filtration targets from drying out.

While the present invention has been thoroughly described so far by way of preferred embodiments with reference to the accompanying drawings, variations and modifications will be apparent to those skilled in the art. It should be understood that the variations and modifications made without departing from the scope hereinafter claimed are also embraced by the present invention.

The filtration filter according to the present invention helps keep a filtration target from drying out and is thus particularly useful for taking out, by filtration, cells or any other substance derived from living organisms.

REFERENCE SIGNS LIST 1 filtration filter
2 filter portion
2a first principal surface
2b second principal surface
3 frame portion
21 through-hole
22 filter substrate
22a, 22b projection
22aa, 22ba inner face
22ab, 22bb outer face
22ac, 22bc first linear section
22ad, 22bd second linear section
22ae, 22be corner section
23 liquid
24 reservoir part
41 substrate
42 sputter-deposited film
43 photoresist film
43A photoresist image
44 metal

The invention claimed is:

1. A filtration filter comprising:
a filter substrate defining a plurality of through-holes extending from a first principal surface to a second principal surface opposite the first principal surface; and
a plurality of projections that each form a loop that extends along a periphery of a respective through-hole of the plurality of through-holes that is adjoined by the projection, the plurality of projections protruding from the first principal surface so as to define a reservoir part with the first principal surface.

2. The filtration filter according to claim 1, wherein the plurality of projections each have an inner face defining the reservoir part, the inner face of each projection being inclined or curved in such a manner that a perimeter of the reservoir part increases with increasing distance from the first principal surface.

3. The filtration filter according to claim 2, wherein the plurality of projections each have an outer face opposite the inner face, the outer face extending from the first principal surface and inclined or curved toward an inside the through-hole that is adjoined by the projection.

4. The filtration filter according to claim 1, wherein the plurality of projections each have an outer face opposite the inner face, the outer face extending from the first principal surface and inclined or curved toward an inside the through-hole that is adjoined by the projection.

5. The filtration filter according to claim 1, wherein, when a cross section of the filtration filter is taken in a direction from the first principal surface to the second principal surface and along a line passing through adjacent through-holes of the plurality of through-holes, a straight line forming a connection between tops of inner faces of projections of the plurality of projections is longer than the second principal surface between the adjacent through-holes.

6. The filtration filter according to claim 1, wherein
when viewed in a plan view from the first principal surface, each of the plurality of projections includes a first linear section, a second linear section, and a corner section that connects an end portion of the first linear section and an end portion of the second linear section, and
a height of the corner section as measured from the first principal surface is less than a height of the first linear section and is less than a height of the second linear section.

7. The filtration filter according to claim 1, wherein the second principal surface is flat.

8. The filtration filter according to claim 1, wherein the filtration filter comprises a porous metallic membrane.

9. The filtration filter according to claim 1, wherein a distance between the first principal surface and a crest of each of the plurality of projections is not less than 10 nm and not more than 10 times a thickness of the filter substrate.

* * * * *